United States Patent [19]

Aldwin et al.

[11] Patent Number: 4,894,226

[45] Date of Patent: Jan. 16, 1990

[54] SOLUBILIZATION OF PROTEINS FOR PHARMACEUTICAL COMPOSITIONS USING POLYPROLINE CONJUGATION

[75] Inventors: Lois Aldwin, San Mateo; Danute E. Nitecki, Berkeley, both of Calif.

[73] Assignee: Cetus Corporation, Emeryville, Calif.

[21] Appl. No.: 931,197

[22] Filed: Nov. 14, 1986

[51] Int. Cl.4 .................... A61K 37/02; A61K 45/02
[52] U.S. Cl. .................... 424/85.2; 424/85.1; 424/85.4; 424/85.6; 424/88
[58] Field of Search .................. 424/85, 85.2, 85.1, 424/85.4–85.7, 88; 514/12; 530/351

[56] References Cited

U.S. PATENT DOCUMENTS

| | | | |
|---|---|---|---|
| 3,788,948 | 1/1974 | Kagedal et al. | 424/85 |
| 4,055,635 | 10/1977 | Green et al. | 424/85 |
| 4,088,538 | 5/1978 | Schneider | 424/85 |
| 4,261,973 | 4/1981 | Lee et al. | |
| 4,414,147 | 11/1983 | Klibanov et al. | 424/85 |
| 4,496,689 | 1/1985 | Mitra | 424/85 |
| 4,716,120 | 12/1987 | Tsay et al. | 424/88 |

FOREIGN PATENT DOCUMENTS 0147761 7/1985 European Pat. Off. .
0154316 9/1985 European Pat. Off. .
56-088794 7/1981 Japan .
57-163318 10/1982 Japan .

OTHER PUBLICATIONS

K. Wetz et al, *Synthesis of Long, Hydro., Protein–Crosslinking Reagents*, 80:473.
E. Mozes et al., *Antibody Response of Inbred Mouse Strains to Ordered* (1974), *Tetrapeptides of Tyrosine and Glutamic Acid Attached to Multi*, etc., 81:289 (1974).
Morimoto et al., *J. Pharm. Dyn.*, 7, 688–698 (1984).
Tsukada et al., *JNCI* (1984) 73:721–729.

*Primary Examiner*—Blondel Hazel
*Attorney, Agent, or Firm*—Philip L. McGarrigle; Janet E. Hasak; Albert P. Halluin

[57] ABSTRACT

A pharmaceutical composition is prepared wherein a biologically active conjugated protein is dissolved in an aqueous carrier medium in the absence of a solubilizing agent. The unconjugated protein, which is not readily water-soluble at pH 6–8 without such solubilizing agent, is covalently conjugated to polyproline via a flexible spacer arm and exhibits substantial biological activity.

16 Claims, 1 Drawing Sheet

SOLUBILIZATION OF PROTEINS FOR PHARMACEUTICAL COMPOSITIONS USING POLYPROLINE CONJUGATION

BACKGROUND OF THE INVENTION

This invention relates to a chemical modification of biologically active proteins which alters the chemical and/or physiological properties of these proteins. More specifically, this invention relates to selective conjugation of a poorly water-soluble protein to a modified polyproline homopolymer to render the protein more soluble at physiological pH.

Many heterologous proteins produced in microbial host cells are found as poorly soluble material in refractile bodies. Examples of heterologous proteins which form refractile bodies in commonly found culture conditions include interleukin-2 (IL-2), interferon-$\beta$ (IFN-$\beta$), feline leukemia virus (FeLV) envelope protein, human growth hormone (hGH), bovine growth hormone (bGH), porcine growth hormone (pGH), and certain proteins coated or fused with a virus such as FMD virus. In addition, many of these proteins are hydrophobic in nature and tend to stick to materials and to themselves (i.e., aggregate) rather than remain in solution. Also, many of these recombinant proteins are unglycosylated, whereas their native counterparts are water-soluble, glycosylated molecules. Modifications of these proteins that might alter their solubility properties would be desirable to increase production yields of these proteins as well as to facilitate their forrulation for therapeutic use.

The use of polypeptides in circulatory systems for the purpose of producing a particular physiological response is well known in the medicinal arts. A limitation to the potential therapeutic benefit derived from the clinical use of polypeptides is their ability to elicit an immune response in the circulatory system. This immune 30 response may be caused by aggregates in the material prior to injection as described by R. Illig (1970), *J. Clin. Endrocr.*, 31, 679–688, W. Moore (1978), *J. Clin. Endrocrinol. Metab.*, 46, 20–27 and W. Moore and P. Leppert (1980), *J. Clin. Endrocrinol. Metab.*, 51, 691–697. This response involves the production of antibodies to the polypeptides by the circulatory system into which they are injected. This antibody production may decrease or eliminate the desired biological function of the polypeptide, sometimes by causing reduced residence time in the circulatory system (reduced half-life) or by modifying the molecule by virtue of the antibody-polypeptide interaction.

Modification of these potentially useful therapeutic polypeptides, per se, may increase the half-life of the polypeptides. The mechanism for this increase is not clear; it does not involve the immune system, but it may be due to clearance or protein turnover mechanisms.

The problems of immunogenicity and short half-life in circulation set forth hereinabove and other undesirable properties of certain proteins are well recognized and various modifications of polypeptides have been undertaken to solve them. These include the modification of proteins with substantially straight chain polymers such as polyethylene glycol (PEG) or polypropylene glycol (PPG).

For example, U.S. Pat. No. 4,055,635 discloses pharmaceutical compositions comprising a water-soluble complex of a proteolytic enzyme linked covalently to a polymeric substance such as polysaccharides.

U.S. Pat. No. 4,088,538 discloses a reversibly soluble enzymatically active polymer enzyme product comprising an enzyme covalently bonded to an organic polymer such as polyethylene glycol.

U.S. Pat. No. 4,415,665 discloses a method of conjugating an organic ligand containing at least one primary or secondary amino group, at least one thiol group and/or at least one aromatic hydroxy group (described in col. 3, lines 19–36) to a polymeric carrier with at least one hydroxyl group (described in col. 2, lines 42–66).

U.S. Pat. No. 4,496,689 discloses a covalently attached complex of alpha-1-proteinase inhibitor with a polymer such as PEG or methoxypolyethylene glycols.

U.S. Pat. No. 3,619,371 discloses a polymeric matrix having a biologically active substance chemically bound thereto.

U.S. Pat. No. 3,788,948 discloses use of organic cyanate pounds to bind proteins to polymers.

U.S. Pat. No. 4,055,635 discloses pharmaceutical compositions of a proteolytic enzyme linked covalently to a polymeric substance.

JP 5792435 published November 26, 1982 discloses modified polypeptides where all or part of the amino groups are substituted with a polyethoxyl moiety. DE 2312615 published September 27, 1973 discloses conjugating of polymers to compounds containing hydroxy or amino groups.

EP 147,761 discloses a covalent conjugate of alpha-1-proteinase inhibitor and water-soluble polymer, where the polymer may be polyethylene glycol.

EP 154,316, published September 11, 1985 to Takeda Chemical Industries, Ltd., discloses and claims chemically modified lymphokines such as IL-2 containing PEG bonded directly to at least one primary amino group of a lymphokine.

U.S. Pat. No. 4,414,147 describes rendering-interferon less hydrophobic by conjugating it to an anhydride of a dicarboxylic acid such as poly(ethylene succinic anhydride).

Copending U.S. Ser. No. 866,459 filed May 21, 1986 discloses-conjugation of PEG and polyoxyethylated polyols to such proteins as interferon-$\beta$, interleukin-2 and immunotoxins.

Copending U.S. Ser. No. 879,456 filed June 27, 1986 discloses conjugation of heparin fragments to such proteins as interforon-$\beta$, interleukin-2, and immunotoxins.

Chemotherapeutic agents such as melphalan have been conjugated through a carbodiimide-catalyzed reaction to poly(amino-acids) to yield drug carriers that may attain sustained release in cancer chemotherapy. See Morimoto et al., *J. Pharm. Dyn.*, 7, 688–698 (1984).

Copending U.S. Ser. No. 648,759 filed Sept. 7, 1984, discloses a toxin conjugate for preparing immunotoxins wherein the cloned bridge between the toxin portion and the antibody portion is a sequence of 4–6 proline residues bracketed by two flexible amino acid sequences. The bridge is designed to be non-hydrophobic to maintain or improve water solubility of the immunotoxin.

The Morimoto et al. article and the other references do not disclose how to conjugate polyproline to recombinant proteins such as IL-2 and IFN-$\beta$ that are not very soluble in an aqueous medium at physiological pH. Furthermore, it is not a priori possible to predict which selected proteins would be favorably responsive, e.g., have good biological activity, to treatment with polyproline, due to the vast difference in physical and biological properties among proteins.

SUMMARY OF THE INVENTION

Accordingly, the present invention provides for modifying those proteins that are poorly soluble in water under ambient conditions at pharmaceutically acceptable pH ranges to render them more soluble in aqueous buffer under such conditions. This modification may be mimicking glycosylation of the protein, thereby surprisingly rendering the protein substantially more soluble. This modification also avoids addition of extraneous solubilizing additives such as detergents or denaturants to keep the protein in solution. The modified protein retains most of the biological activity of the unmodified-protein, both initially and over time.

As secondary advantages, the modification under some conditions may improve the physiological half-life of the protein and may decrease its immunogenicity by reducing or eliminating aggregation of the protein or by masking antigenic determinants. Also, one would expect polyproline chain to be less susceptible to common serum proteases that are specific for lysine and/or arginine, than proteins or polymers containing these residues.

More specifically, the present invention is directed to a pharmaceutical composition comprising a nontoxic, inert, pharmaceutically acceptable aqueous carrier medium in which is dissolved a biologically active protein covalently conjugated (bonded) via a flexible spacer arm to polyproline, wherein said protein in its unconjugated form is not readily soluble in said aqueous carrier medium at pH 6–8 in the absence of a solubilizing agent.

Preferably the protein is selected from the group consisting of those interferons, interleukins, colony stimulating factors, and immunotoxins that are not readily soluble in water. More preferably, the protein is human recombinant interleukin-2 or human recombinant interferon-$\beta$ that is not readily soluble in water and the polyproline is coupled to the protein via an amide linkage formed from the 1-hydroxy-2-nitrobenzene-4-sulfonate active ester or the N-hydroxysuccinimide or N-hydroxysulfosuccinimide ester attached to the N-terminus of the polyproline.

Another aspect of this invention resides in a process for preparing a pharmaceutical composition comprising:

(a) preparing polyproline attached to a flexible spacer arm that is in turn attached to a terminal reactive group;

(b) reacting a biologically active protein that is not readily water soluble with the terminal reactive group of said polyproline so as to provide a more water-soluble, biologically active, covalently conjugated protein; and (c) formulating said protein in a non-toxic, inert, pharmaceutically acceptable aqueous carrier medium.

The spacer arm herein is attached to the polyproline, on the one hand, and the protein, on the other hand. It is not of the type described in copending U.S. Ser. No. 648,759, supra, wherein the spacer arm includes a cloned sequence of 4–6 prolines and bridges the toxin and antibody.

DESCRIPTION OF THE PREFERRED EMBODIMENTS

As used herein, the term "not readily water-soluble" as describing the proteins herein refers to those proteins which are not very soluble in water or an aqueous medium under ambient conditions of room temperature and atmospheric pressure at a pH of between about 6 and 8, i.e., at about neutral or physiological pH. The modification herein acts to increase the solubility of such proteins when they are subjected to such physiological conditions. For purposes herein, ready solubility may be tested by (1) turbidity, as measured by spectrophotometric means, and (2) S value, as measured by ultracentrifugation, wherein soluble monomeric protein is evidenced by a low sedimentation rate and aggregated material by a much larger sedimentation rate. The exact numbers that would indicate solubility for each of these tests will depend on the type of buffer in which the protein is formulated, the pH of the buffer, and the ionic strength of the buffer.

The types of proteins that meet this definition and therefore can be employed herein include such proteins as, for example, any enzymes, lymphokines and cytotoxins that are not readily soluble in water in either their native form or recombinant form (from any host). Certain interferons (IFN-$\beta$, in particular), interleukins (e.g., IL-1, IL-2, IL-3, IL-4), colony stimulating factors (e.g., CSF-1, CSF-G, CSF-GM) and immunotoxins fit this criterion. For example, CSF-1 is readily soluble as a native molecule, insoluble as recombinant CSF-1 from E. coli, but readily soluble as recombinant CSF-1 from monkey cells. Different hosts produce different products with regard to S-S content and type of glycosylation, etc. Preferred proteins herein are human interferon-B and interleukin-2 produced recombinantly from E. coli, one or more of the colony stimulating factors, and one or more immunotoxins.

The proteins herein may be native or obtained by recombinant techniques, and may be from any source, including mammalian sources such as, e.g., mouse, rat, rabbit, primate, pig, and human, provided they meet the solubility criterion specified herein. Preferably such proteins are derived from a human source, and more preferably are recombinant, human proteins from microbial hosts.

The term "recombinant $\beta$-interferon" (IFN-$\beta$) refers to fibroblast interferon having comparable biological activity to native IFN-$\beta$ prepared by recombinant DNA techniques as described in the art. In general, the gene coding for interferon is inserted into a cloning vector for cloning purposes and then into an expression vector, which is used to transform a host organism. The host organism is preferably a microorganism, and most preferably E. coli. The host organism expresses the foreign interferon gene under certain conditions to produce IFN-$\beta$. More preferably, the IFN-$\beta$ is a mutein as described in U.S. Pat. No. 4,588,585, in which the cysteine normally occurring at position 17 of the wild-type or native molecule has been replaced by a neutral amino acid such as serine or alanine. Most preferably, the IFN-$\beta$ mutein is IFN-$\beta_{ser17}$ or a mutein wherein any combination of up to 5 of the first five N-terminal amino acid residues are deleted.

The term "recombinant interleukin-2" (IL-2) refers to interleukin-2. having comparable biological activity to native-sequence IL-2 prepared by recombinant DNA techniques as described e.g., by Taniguchi et al., *Nature*, 302:305-310 (1983) and Devos, *Nucleic Acids Research*, 11:4307-4323 (1983) or mutationally altered IL-2 as described by Wang et al., *Science*, 224:1431-1433 (1984). In general, the gene coding for IL-2 is cloned and then expressed in transformed organisms, preferably a microorganism, and most preferably E. coli. The host organism expresses the foreign gene to produce IL-2 under expression conditions. More preferably the IL-2 is a mutein as described in U.S. Pat. No. 4,518,584, in which the cysteine normally occurring at position 125 of the wild-type or native molecule has been replaced by a neutral amino acid such as serine or alanine. alternatively or conjunctively, the IL-2 mutein may be one as described in copending U.S. application Ser. No. 810,656 filed Dec. 17, 1985, the disclosure of which is incorporated herein by reference, in which the methionine normally occurring at position 104 of the wild-type or native molecule has been replaced by a neutral amino acid such as alanine.

Preferably, the IL-2 is a protein produced by a microorganism that has been transformed with the human cDNA sequence or a modified human cDNA sequence of IL-2 that encodes a protein with an amino acid sequence at least substantially identical to the amino acid sequence of native human IL-2, including the disulfide bond of the cysteines at positions 58 and 105, and has biological activity that is common to native human IL-2. Substantial identity of amino acid sequences means the sequences are identical or differ by one or more amino acid alterations (additions, substitutions, deletions) which do not cause an adverse functional dissimilarity between the synthetic protein and native human IL-2. Examples of IL-2 proteins with such properties include those described by Taniguchi et al., supra; Devos, supra; European Patent Publication Nos. 91,539 and 88,195; U.S. Pat. No. 4,518,584, supra, and copending U.S. application Ser. No. 810,656 filed Dec. 17, 1985, supra, covering, e.g., IL-2$_{ala104ser125}$. Most preferably, the IL-2 is ser$_{125}$IL-2, des-ala$_1$ser$_{125}$IL-2, des-ala$_1$IL-2, des-ala$_1$ala$_{104}$IL-2, des-ala$_1$ala$_{104}$ser$_{125}$IL-2, where "des-ala$_1$" indicates that the N-terminal alanyl residue of the IL-2 has been deleted, or an IL-2 mutein wherein any combination of up to 5 of the first five N-terminal amino acid residues of the native IL-2 are deleted.

The precise chemical structure of the proteins herein will depend on a number of factors. As ionizable amino and carboxyl groups are present in the molecule, a particular protein may be obtained as an acidic or basic salt, or in neutral form. All such preparations that retain their bioactivity when placed in suitable environmental conditions but are not readily soluble in water are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the bioactivity of the protein is not destroyed and the water solubility of the protein not greatly increased. It is expected, of course, that such modifications may quantitatively or qualitatively affect the bioactivity by either enhancing or diminishing the activity of the protein in the various assays.

Often hydrophobic recombinant proteins such as IL-2 and IFN-$\beta$ produced from transformed host cells containing recombinant DNA occur as "precipitates" inside the cell as opposed to being soluble in the cell culture medium. The intracellularly produced protein must be separated from the cellular debris and recovered from the cell before it can be formulated into a purified biologically active material. Commonly owned U.S. Pat. No. 4,748,234, issued March 31, 1988, entitled "Process for Recovering Refractile Bodies Containing Heterologous Proteins From Microbial Hosts" to W. Hanisch et al., the entire disclosure of which is incorporated herein by reference, discloses a process for isolating such a refractile material. In this process the cell membrane of the transformed host microorganism is disrupted, greater than 99% by weight of the salts is removed from the disruptate, the desalted disruptate is redisrupted, a material, preferably a sugar such as sucrose, is added to the disruptate to create a density or viscosity gradient in the liquid within the disruptate, and the refractile material is separated from the cellular debris by high-speed centrifugation, i.e., at about 10,000 to 40,000$\times$g. Preferably, the salts are removed from the disruptate by diafiltration or centrifugation and sucrose is added to increase the density of the liquid to about 1.1 to 1.3 g/ml.

The "particle pellet" obtained by centrifugation may then be solubilized, as when sodium laurate is the primary solubilizing agent, or may be solubilized under reducing conditions, extracted organically from the aqueous medium, as by using 2-butanol, and precipitated with an acid and centrifuged to produce a "final pellet or paste."

In the next step of purification, either the "particle pellet" or "the final pellet or paste" containing the refractile bodies is solubilized with a denaturant such as sodium dodecyl sulfate, optionally in the presence of a reducing agent such as dithiothreitol. The resulting suspension is then optionally centrifuged, and if a reducing agent was not present during solubilization, is treated under reducing conditions.

Then, the supernatant fluid containing the protein is treated to isolate the protein. The protein is separated from the supernatant fluid by appropriate means such ad reverse-phase high pressure liquid chromatography (RP-HPLC) and/or gel filtration chromatography. After such separation, the protein is preferably oxidized to ensure the production of high yields of recombinant protein in a configuration most like its native counterpart. Such oxidation is described in U.S. Pat. No. 4,530,787 to Z. Shaked et al., the disclosure of which is incorporated herein by reference. The oxidation may also be carried out by reacting an aqueous solution containing a solubilized form of the protein at a pH between about 5.5 and 9 in the presence of air with at least an effective amount of an oxidation promoter containing a Cu$^{+2}$ cation, as described in U.S. Pat. No. 4,572,798 to K. Koths et al., the disclosure of which is incorporated herein by reference. The preferred oxidation promoter or oxidant is CuCl$_2$ or (o-phenanthroline)$_2$ Cu$^{+2}$.

After oxidation, the protein may optionally be desalted and purified further by RP-HPLC, dilution/diafiltration, S-200 gel filtration chromatography, and/or ultrafiltration techniques before modification with polyproline as described further hereinbelow. At least in the case where the 4-hydroxy-3-nitrobenzene sulfonate ester is employed in the modification, the presence of denaturants (such as, e.g., SDS, guanidinium HCl, or urea for IL-2 solubility) does not affect the chemical modification. The polyproline modification may, however, be carried out at any step after the heterologous protein has been isolated in sufficiently pure form to be biologically active for therapeutic purposes. The point at which the modification will occur will depend on the ultimate purity of the protein required for the final pharmaceutical formulation and use.

The IL-2 may be purified as described in U.S. Pat. No. 4,569,790 issued Feb. 11, 1986, the disclosure of which is incorporated herein by reference. The preferred IL-2 for clinical use is purified to have an IL-2 content of at least about 95% as determined by reducing SDS-PAGE analysis, an endotoxin content of less than about 0.1 ng/mg of IL-2, and to be substantially free of pyrogens as determined by the U.S.P. rabbitpyrogen test at a dosage of $3.3 \times 10^5$ U/kg.

The term "colony stimulating factor" (CSF) as used herein refers to factors that in low concentration stimulate the growth and development of bone marrow progenitor cells into mature cells such as granulocytes and/or macrophages. There are at least four subclasses of human CSF proteins that can be defined according to the types of cells found in the resultant colonies. All of these subclasses are included in the definition herein.

One subclass of CSF, called CSF-1, stimulates colonies containing predominantly macrophages. Other subclasses include those producing colonies that contain both neutrophilic granulocytes and macrophages (CSF-GM) and that contain exclusively neutrophilic granulocytes (CSF-G). The CSF-1 protein particularly preferred herein is te recombinant CSF-1 described in abandoned U.S. Pat. No. application Ser. No. 876,819 filed June 20, 1986, the disclosure of which is incorporated herein by reference. A continuation-in-part application of Ser. No. 876,819 was filed Feb. 9,1988 and assigned Ser. No. 07/157,094.

The term "immunotoxin" as used herein to apply to the third class of proteins refers to a conjugate of an antibody and a cytotoxic moiety. The cytotoxic moiety of the immunotoxin includes a cytotoxic drug or an enzymatically active toxin of bacterial or plant origin or an enzymatically active fragment ("A chain") of such a toxin. Examples of enzymatically active toxins and fragments thereof include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and enomycin. Ricin A chain, nonbinding active fragments of diphtheria toxin, abrin A chain, and PAPII are preferred. Most preferred is the ricin A chain, which is modified by reaction with the derivatized polyproline.

The antibodies employed in the immunotoxin are preferably monoclonal antibodies directed against a specific pathological condition such as, e.g., cancers such as breast, prostate, colon or ovarian cancer, melanoma, myeloma, etc.

Conjugates of the antibody and cytotoxic moiety may be made using a variety of bifunctional protein modifying reagents. Examples of such reagents include N-succinimidyl-3-(2-pyridyldithio) propionate (SPDP), iminothiolane (IT), bifunctional derivatives of imidoesters such as dimethyl adipimidate hydrochloride, active bifunctional esters such as disuccinimidyl suberate, aldehydes such as glutaraldehyde, bis-azido compounds such as bis (p-azidobenzoyl) hexanediamine, bis-diazonium derivatives such as bis-diazotized benzidine, diisocyanates such as tolylene-2,6-diisocyanate, and bis-active fluorine compounds such as 1,5-difluoro-2,4-dinitrobenzene.

The term "covalently conjugated" as used herein to apply to the protein refers to proteins which are covalently bonded via one or more of the amino acid residue side chains of the protein, depending mainly on the reaction conditions. While the residues may be any reactive amino acids on the protein, such as cysteines or the N-terminal amino acid group, preferably the residue is the reactive amino side chain of lysine, which is linked, via appropriately derived chemical moieties, to polyproline.

According to the process of this invention, the three types of proteins described above, which are not readily soluble in water, are rendered more soluble in an aqueous carrier medium, preferably at a pH of about 5 to 8, more preferably about 6–8 and most preferably, 6.5–7.8, without use of solubilizing agents, by modifying the proteins through conjugation to polyproline.

If the protein is reacted through its lysine residues, the pH of the reaction is preferably about 6.5–8.5, more preferably 7.5. The success of such a modification of these proteins cannot be predicted from earlier use of other polymers to modify various proteins.

The poly-L-proline is obtainable commercially from, e.g., Sigma Chemical Co., St. Louis, MO 63178, with a molecular weight ranging from 1000 to over 30,000 daltons. The polyproline need not have a defined molecular weight, but it is preferred that the molecular weight be between about 1000 and 100,000, more preferably between 2000 and 40,000, depending, for example, on the particular protein employed. Preferably the polyproline is a homopolymer of L-proline.

The protein is conjugated to the polyproline via a N-terminal reactive group on the spacer arm that selectively reacts with, or provides a site for linking or conjugating to, one or more free amino groups or other reactive groups on the protein. The terminal reactive group is at or near the terminus of the spacer arm and is preferably an active ester linkage of carboxylic acid if the amino group on the protein is being reacted therewith. A further requirement for the reaction is that a flexible spacer arm be present between the N-terminus of the polyproline molecule and the terminal reactive group of the spacer arm. For example, the reaction:

where polypro-N is described above and IL-2-NH2 is IL-2, proceeds to form the reaction product conjugate:

where a leaving group of the active ester.

Furthermore, the reaction:

where polypro-N represents polyproline with its N-terminus modified and IL-2-NH represents IL-2 with some amino groups modified, may yield the product as well.

Another reaction that may yield the product is the reverse of the above reaction, namely:

where polypro-N represents polyproline with its N-terminus modified and IL-2-NH represents IL-2 with some amino groups modified.

The length and nature of the flexible spacer arm depends, for example, on the molecular weight of the polyproline, the type of protein employed, and the reaction conditions utilized. In functional terms, the words "flexible spacer arm" refer to an organic moiety that is chemically non-reactive with the protein and polyproline ad is of sufficient length (at least five carbon atoms in the straight (main) chain) to permit the reaction to occur. Preferably it is also water soluble and not immunogenic. Its purpose is to connect the polyproline with its terminal reactive group while avoiding interaction between the two or interference with the protein so that the reaction can take place. The flexibility signifies that the spacer arm is not comprised of a rigid structure that cannot rotate readily during the reaction and permits three-dimensional movement of the protein and the polyproline portions of the molecule. Preferably, the spacer arm comprises a straight chain which contains at least seven total atoms, and will have few if any side chains.

The size limits of the spacer arm will be determined by the types of atoms contained therein and by solubility considerations. The optimum molecular weight for the spacer arm is generally about due to synthesis considerations.

The atoms that may be employed in the straight chain of the spacer arm include carbon, oxygen, nitrogen, sulfur, and other substitutes therefor that will be inert to the conjugation reaction. The linkage of these atoms may include any bonds such as, e.g., carbon-carbon single bonds, carbon-carbon double bonds, carbon-nitrogen single bonds, carbon-oxygen single bonds, and carbon-sulfur single bonds. Generally, however, the straight chain will consist of a hydrocarbon chain of $-(CH_2)-$ groups or of $-(CH_2)_xY-$ groups where Y is a polar group containing N, O, or S atoms, including amide groups, and x is an integer of at least 1. Preferably, the straight chain contains at least one polar group to ensure that the spacer arm will be hydrophilic so that it will be extended rather than coiled in aqueous solution.

Although the main chain may contain one or more branches such as alkyl groups, it is preferred that the main chain be minimally substituted to avoid steric hindrance and solubility problems. Between the N-terminus of polyproline and the reactive terminal group may be aromatic or aliphatic rings that do not adversely affect the flexibility and solubility properties of the spacer arm.

where a is at least 1, and is preferably 5. For enhanced solubility and flexibility, the chain may contain where x is 2–4, y is 2–4, and z is 2–4. One species of this latter compound has the formula:

Such molecule can be chemically derivatized to provide appropriate reactive functions to crosslink polyproline and a protein together.

This crosslinker product can be used to couple polyproline to a protein in several ways. For example, it can be reacted with polypro-N-CH$_2$CH$_2$-SH, yielding:

This product is then reacted with IL-2-NH$_2$, yielding:

The crosslinker product can also be reacted with polypro-N, yielding:

or and this product reacted in a subsequent step with yielding:

Thus, the spacer arm may also be:

where a is at least 1, x is 2–4, Y is 2–4, z is 2–4, and n is 1–10.

The conjugate of polyproline and spacer arm with terminal reactive group may be prepared by any suitable method used to conjugate chemical moieties. In one preferred embodiment, the conjugate is prepared by first preparing 3-(2-pyridyldithio)propionyl-1-hydroxy-2-nitrobenzene-4-sulfonate ester (HNSA) as described in Example I below, and in Nitecki et al., *High-Technology Route to Virus Vaccines* (American Society for Microbiology (1986) in a chapter entitled "Novel Agent for Coupling Synthetic Peptides to Carariers and Its Application," the disclosure of which is incorporated herein by reference.

This reagent is then purified to remove excess small reagents by any suitable means. Such means include, for example, differential precipitation, HPLC, thin-layer chromatography, G-25 Sephadex column filtration, and the like. The purified reagent is then reacted with the polyproline to produce a compound of the formula:

where polypro-N is defined above. This reagent is reduced with a reducing agent such as dithiothreitol to produce:

This reagent is in turn reacted with prepared as described in Example I below and in D. Nitecki et al., supra, to produce the product:

This product is in turn reacted with the protein, to produce, in the case of IL-2, for example:

where IL-2-NH represents IL-2 with a terminal amine group.

In an alternative modification, polyproline can be reacted with SPDP, an N-hydroxysuccinimide ester manufactured by Pharmacia, or a N-hydroxysulfosuccinimide ester of 3-(2-pyridyldithio)propionic acid. The resulting reagent is then reacted with, for example, N-maleimido-6-aminocaproyl-HNSA ester. The product of that reaction is reacted directly with the protein.

For the reaction of modified polyproline with the protein, it is recommended that generally about 1 to 5 moles, preferably 3 moles, of modified polyproline per mole of protein, depending on the desired degree of substitution, is employed. The desired degree of substitution in turn depends on the biological activity of the resulting conjugate and other desirable properties such as solubility and half-life. Preferably some of the biological activity of the native protein is retained, more preferably 100% is retained, and most preferably over 100% of the biological activity is achieved.

The covalent protein modification reaction may take place under any suitable reaction conditions generally used for reacting biologically active materials with activated polymers, preferably at about pH 6.5–8.5, if the reactive groups on the protein are lysine groups. If the HNSA ester is employed, the presence of SDS or urea does not affect the modification reaction.

The protein thus modified is then formulated in a non-toxic, inert, pharmaceutically acceptable aqueous carrier medium, preferably at a pH of about 5 to 8, more preferably 6–8. For in vitro applications, as for immunotoxins used for diagnostic purposes, the modes of administration and formulation are not critical. Aqueous formulations compatible with the culture or perfusion medium will generally be used. When used in vivo for therapy, the sterile product will consist of a mixture of protein dissolved in an aqueous buffer in an amount which will provide a pharmaceutically acceptable pH when the mixture is reconstituted. A water-soluble carrier such as mannitol may optionally be added to the medium, as well as an excipient such as, e.g., water, Ringer's solution, Hank's solution, saline, glycerol, dextrose solutions and the like. The currently formulated unmodified IL-2 is stable for at least two years at 4° C.

The dosage level of protein in the formulation will depend on the in vivo efficacy data obtained after preclinical testing and will depend mainly on the protein employed and ultimate use.

If the formulation is lyophilized, the lyophilized mixture may be reconstituted by injecting into the vial a conventional parenteral aqueous solvent such as, e.g., distilled water.

The reconstituted formulation prepared as described above is suitable for parenteral administration to humans or other mammals in therapeutically effective amounts (i.e., amounts which eliminate or reduce the patient's pathological condition) to provide therapy thereto, the type of therapy being dependent on the type of protein. For example, IL-2 therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell mediated anti-tumor activity.

In an alternative to direct administration of IL-2, the IL-2 may be administered in an adoptive immunotherapy method, simultaneously with isolated, lymphokine-activated lymphocytes, in a pharmaceutically acceptable carrier, where the lymphocytes have antitumor activity when administered with the IL-2 to humans suffering from the tumor. This method is described more fully in copending U.S. application Ser. No. 763,657 entitled "IL-2/Adoptive Immunotherapy" filed Aug. 8, 1985 (NTIS), and by S. Rosenberg et al., *New England Journal of Medicine* (1985), 313:1485–1492, the disclosures of which are incorporated herein by reference. In another alternative, described in S. Rosenberg et al., *Science,* 233:1318–1321 (1986), tumor-infiltrating lymphocytes (TIL) expanded in IL-2 may be adoptively transferred for the therapeutic treatment, particularly in combination with cyclophosphamide. The TIL approach of Rosenberg et al., the disclosure of which is incorporated herein by reference, may also be used herein.

IFN-$\beta$ therapy is appropriate for anti-cancer, anti-viral and anti-psoriasis treatment. Specific cancers against which IFN-$\beta$ has shown some efficacy include lymphoma, myeloma, hairy-cell leukemia and some viral diseases including venereal warts and rhinoviruses.

CSF therapy is appropriate as an adjunct to chemotherapy. In fact, any subject suffering from immunosuppression, whether due to chemotherapy, bone marrow transplantation, or other accidental forms of immunosuppression such as disease (e.g., AIDS), would benefit from the availability of CSF for pharmacological use. CSF is also useful in the treatment of neoplasms and infections, and stimulates production of interferons and myeloid CSF.

Immunotoxin therapy is appropriate for diseases against which the targeted antibody is effective, usually cancer. In particular, immunotoxins are being targeted for such cancers as breast cancer.

The dose and dosage regimen of the immunotoxin will depend, for example, upon the pharmacokinetics of the drug, the nature of the cancer (primary or metastatic) and its population, the molecular weight of the polyproline, the characteristics of the particular immunotoxin, e.g., its therapeutic index, the patient, and the patient's history. The dose and dosage regimen of the IL-2, IFN-$\beta$, and CSF will similarly depend, for example, on the characteristics of the IL-2, IFN-$\beta$, and CSF, the patient and the patient's history. For example, different modified IL-2 proteins are expected to have different pharmacokinetic and therapeutic properties that are L. advantageous for different routes of administration. A long-acting drug might only be administered every 3–4 days, every week or once every two weeks. The clearance rate can be varied to give ultimate flexibility to fit the particular need of the patient by changing, e.g., the size of the polyproline attached.

In the following examples, which illustrate the invention further, all parts and percentages are by weight unless otherwise noted, and all temperatures are in degrees Celsius.

EXAMPLE I

Preparation and Characterization of Conjugate of Interleukin-2 (IL-2) and Polyproline Poly-L-proline obtained from Sigma Chemical Co., St. Louis, MO was determined by end group reactivity to have an average molecular weight of 7000 after dialysis.

3-(2-Pyridyldithio)propionyl-4-hydroxy-3-nitrobenzene sulfonic ester was prepared by mixing together one molar equivalent (1.63 g) of 1-hydroxy-2-nitrobenzene-4-sulfonic acid sodium salt (HNSA) with one molar equivalent (1.4 g) of dicyclohexylcarbodiimide and one molar equivalent (1.45 g) of 3-(2-pyridyldithio)propionic acid in 70 ml of dimethylformamide (DMF) at room temperature for 16 hours until a white dicyclohexyl urea precipitate appeared. The precipitate was filtered and the mother liquor was concentrated in vacuo to a small volume (about 10 ml). Diethyl ether, 300 ml, was added to this concentrated solution. A yellow oil precipitated from solution upon the addition of the diethyl ether. The precipitate was collected by filtration and gave a yield of 1.97 g of crude product.

The solid was analyzed to contain 45% 3-(2-pyridyldithio)propionyl-HNSA ester together with 55% of free HNSA.

The analysis consisted of dissolving a small amount of the crude active ester mixture in phosphate buffer at pH 7.0 and measuring absorbance at 406 nm; this reading provides the amount of unreacted free HNSA which is the contaminating material in the HNSA ester preparation. Addition of very small amounts of concentrated strong base (such as 5N NaOH) instantly hydrolyzed the ester formed and a second reading was taken. Subtraction of the first reading from the second yields the amount of ester in the original material.

For purification purposes, the crude ester was dissolved in DMF and placed on a LH20 Sephadex column and eluted with DMF. The ester was separated from the contaminating free HNSA. The progress of purification was monitored spectrophotometrically. Pure solid ester was obtained by precipitation with ether.

The product of this purification was reacted with the polyproline by reacting 10 mg of polyproline dissolved in 1.5 ml of a 0.1M phosphate buffer at pH 7.5 with 2.6 mg of the purified ester at room temperature. Twenty μl aliquots were removed from the solution at timed intervals and were each diluted into 1.0 ml of 0.01M phosphate buffer at pH 7.0. The spectrum of each diluted aliquot was recorded using a spectrophotometer to monitor the absorbance at 406 nm. After the initial absorbance at 406 nm was recorded, 50 μl of 5N NaOH was added to hydrolyze the remaining ester, and the higher absorbance at 406 nm was recorded. % Ester remaining was calculated from ($A_{406}$ final-$A_{406}$ initial)/$A_{406}$ final.

The reaction was stopped after 40 minutes by applying the reaction mixture to a desalting Sephadex G-25 column equilibrated with 0.01M phosphate buffer at pH 7.0. The yield of product was found to be 81%. This procedure removed excess of the ester and accompanying small reaction products.

Ten mg of large molecular weight product from the desalting column was reacted with 2.24 mg of dithiothreitol. The resulting product was found to be, in a 100% yield:

This product was purified by G-25 Sephadex column filtration in 0.01M phosphate buffer at pH 6.0. The purified product was reacted with a N-maleimido-6-aminocaproic HNSA ester (mal-sac-HNSA ester) prepared as follows:

One equivalent (2.24 g, 0.01 mole) of HNSA was mixed together - with one equivalent (2.06 g, 0.01 mole) of dicyclohexylcarbodiimide and one equivalent (2.10 g, 0.01 mole) of N-maleimido-6-aminocaproic acid in 25 ml of DMF at room temperature overnight. A white precipitate of dicyclohexyl urea was formed. The precipitate was filtered and 300 ml diethyl ether was added to the mother liquor. After about 10 minutes to four hours a gummy solid that precipitated from the mother liquor was formed. This solid was found to contain 58% of active HNSA ester and 42% of free HNSA by the analysis described above. The product was positively identified as mal-sac-HNSA ester by its reactivity with amines. The yield of the pure ester was estimated to be approximately 30% of theoretical; the purified material consisted of 99% ester.

The ester thus obtained was found to dissolve fully in water and was found to be stable in water for several hours, provided no nucleophiles were added. When placed in 1N ammonia the ester produced the corresponding amide with a portion hydrolyzed to free acid. The purified ester was found to be stable for extended periods when stored desiccated.

The reaction of mal-sac HNSA ester and the polyproline derivative took place as follows: 5.2 mg of the HNSA ester and 8 mg of the polyproline derivative were reacted in 0.01M phosphate, pH 6.0 at room temperature for one hour, and the reaction mixture was lyophilized. Purification of the lyophilized material over a Sephadex LH-20 column using acetic acid solvent removed the unreacted HNSA ester and other small reaction products.

The polyproline-HNSA ester product of this reaction was then lyophilized and reacted with RP-HPLC purified recombinant desT cysteine residue at position 125 is alanyl$_1$ser$_{125}$I L-2 (where the replaced by serine and the N-terminal alanyl residue is deleted), prepared as described in U.S. Pat. Nos. 4,518,584 and 4,530,787, supra, or the post-diafiltered des-ala$_1$ser$_{125}$I L-2 from the production process described hereinabove.

To 11.9 mg of this purified IL-2 in 10.0 ml buffer (0.1M sodium phosphate, pH 7.5; 0.1% SDS) was added 3.5 mg of the polyproline HNSA ester prepared in the previous step. The solution was stirred at room temperature (27° C.) for 30 minutes. The progress of the reaction was monitored as described for reaction of polyproline with 3-(2-pyridyldithio)propionyl-4-hydroxy-3-nitrobenzene sulfonic acid ester.

About 10 mg of the reaction mixture was run on a 500 ml Sephacryl 200 column in 0.1M phosphate buffer pH 7.5, 0.1% SDS at 0.5 ml/minute. The peak fractions were collected. This removed the unmodified IL-2, but not the unreacted polyproline.

For removal of SDS, the above collected pooled peak fractions were chromatographed on a 100 ml G-25 Sephadex column in 10 mM phosphate buffer at pH 7.5 at 1.5 ml/min. The peak fractions were collected and found to be soluble in water without SDS at room temperature and at 4° C. for greater than one week. This column did not remove the unreacted polyproline from the reaction mixture.

The peak fraction from the G-25 column was run on a Mono S cation exchange column at 1 ml/min. The sample was loaded in 50 mM phosphate, pH 5.5, followed by a linear 20-min. gradient to 1M NaCl in 50 mM phosphate, pH 5.5. This column removed the unreacted polyproline, resulting in purified proproline-IL-2 conjugate.

The purified product fractions were found to have a specific bioactivity ranging between $3.85 \times 10^5$ to $1.59 \times 10^7$ units/mg when measured for IL-2 bioactivity (cell proliferation) by the methods generally described by Gillis, S. et al., *J. Immunol.*, 120, 2027-2032 (1978). This compares favorably with a specific activity of unmodified IL-2 of $6.2 \times 10^6$ to $1.1 \times 10^7$ units/mg. Some modified IL-2 fractions had from 147 to 256% of the specific bioactivity of the unmodified IL-2. This is within the range of variation of assay and should not be construed as an improvement in activity.

EXAMPLE II

Preparation and Characterization of Conjugate of Interferon-β (IFN-β) and Polyproline Polyproline was activated as described in Example I and then reacted with IFN-β mutein under the conditions described in Example I for IL-2. The IFN-β rutein was purified, recombinant human IFN-62 where the cysteine residue at position 17 was replaced by a serine residue (ser$_{17}$IFN-β), as described in U.S. Pat. No. 4,588,585, the disclosure of which is incorporated herein by reference.

The IFN-β conjugate was run on an Sephacryl 200 gel filtration column in the presence of SDS or a non-ionic detergent to solubilize the unmodified IFN-β. The sizing chromatography separated the polyproline-IFN-β conjugate from unmodified IFN-β. Some amount of unconjugated polyproline remained in the polyproline-IFN-β preparation. (Other sizing materials could be used for this purpose, in place of the Sephacryl 200 column.)

The peak Sephacryl 200 fractions were chromatographed on an ion exchange Mono S column in the presence of a non-ionic detergent to separate the remaining polyproline from the polyproline-IFN-β conjugate. (It may be possible and preferable to use other cation exchangers and/or to execute the ion exchange step in the absence of detergent.)

The fractions containing polyproline-IFN-β were chromatographed on a G-25 Sephadex desalting column to remove detergent. (Other methods for removing detergent may be employed for this purpose. Further, this desalting step may be executed before the ion exchange chromatography step if the latter can be performed in the absence of a detergent.)

The IFN-β conjugate remained soluble after the desalting step, which removed the SDS. No detergent was found in the desalted fraction.

The IFN-β conjugate was found to have the same activity (i.e., about 1 to $2 \times 10^8$ units/mg) as the unmodified IFN-β rutein starting material, as measured using the cytopathic effect (CPE) IFN-β antiviral assay-method described generally by W. E. Stewart, "The Interferon System," Springer-Verlag, p. 17-18 (1979). The CPE assay functions on the principle that interferon protects cells treated therewith from the effects of virus. Cells more resistant to the virus will survive, whereas those that are sensitive to the virus will experience the cytopathic effect and die.

EXAMPLE III

Preparation and Characterization of Conjugate of Tumor Necrosis Factor (TNF) and Polyproline

A. Preparation of Polyproline-Ester

An active ester of polyproline was obtained as described in Example I.

B. Coupling of Activated Ester to TNF

A mutein of human TNF having the first eight amino acids deleted from the N-terminus was prepared as described in copending U.S. Ser. No. 760,661 filed July 30, 1985, the disclosure of which is incorporated herein by reference. Briefly, TNF was induced from publicly available HL-60 cells and purified and sequenced. Then an intronless sequence encoding human TNF was prepared by producing enriched mRNA, constructing a cDNA library, selecting a probe, and probing the library to recover the sequence. Then an ATG start codon was introduced immediately preceding the GTC sequence encoding N-terminal valine of the mature protein by site-directed mutagenesis. Clones were selected and strands ligated into expression vectors to obtain procaryotic expression of the mutein.

The rutein obtained was in a 0.03M NH$_4$HCO$_3$ buffer. The NH$_4$+ in the sample was completely removed by lyophilization of the sample and by then dissolving the sample in 50 mM phosphate buffer (pH 7.5) and chromatographing over a G-25 Sephadex column. Fractions containing the TNF protein were pooled, and the protein concentration of the resulting pool was determined by absorbance at 280 nm. The pool was again lyophilized. The lyophilized TNF was dissolved in 1.0 ml of deionized water, and protein concentration was determined by the $A_{280}$ nm peak. A TNF concentration of 4.6 mg/ml was determined ($2.71 \times 10^{-7}$ moles/ml).

A total of 7.5 mg of activated polyproline was added to a stirring solution of 1.0 ml of the TNF rutein held at room temperature. The progress of the reaction was monitored spectrophotometrically for the $A_{406}$ characteristic of the released HNSA dianion as described in Example 1. After three hours the reaction mixture was chromatographed over a Sephacryl-200 column in 0.1M phosphate pH 7.0. Higher molecular weight pooled fractions containing the TNF-polyproline conjugate were assayed for TNF bioactivity by the L-929 TNF cytotoxic bioassay described below.

The L-929 assay system is an improved convenient in vitro assay which permits rapid measurement of TNF activity. Its degree of correlation with the *in vivo* tumor necrosis assay of Carsell, et al., Proc. Natl. Acad. Sci. (USA) 1975, 72:3666, supra, is, at present, unknown; however, as it utilizes murine tumor cells specifically, the correlation is expected to be high. The protein designated lymphotoxin in EPO Publication No. 0100641 also gives activity in this assay. The assay is similar in concept to that disclosed in U.S. Pat. No. 4,457,916 which used murine L-M cells and methylene blue staining. However, the L-929 assay has been shown herein to correlate (for HL-60-derived TNF) with human tumor cell line cytotoxicity.

In the L-929 assay system, L-929 cells are prepared overnight as monolayers in microtiter plates. The test samples are diluted two-fold across the plate, UV irradiated, and then added onto the prepared cell monolayers. The culture media in the wells are then brought to 1 µg/ml actinorycin D. The plates are allowed to incubate 18 hours at 37° C. and the plates are scored visually under the microscope. Each well is given a 25, 50, 75 or 100% mark signifying the extent of cell death in the well. One unit of TNF activity is defined as the reciprocal of the dilution at which 50% killing occurs.

The results of the L-929 assay are that the TNF modified with the same polyproline reagent as IL-2 and IFN-$\beta$ had only 1% of the bioactivity of the native TNF. Specifically, the bioactivity of native TNF was measured to be $> 1.1 \times 10^6$ units/mg, whereas the bioactivity of the polyproline-modified TNF was measured to be $3.95 \times 10^4$ units/mg.

EXAMPLE IV

Preparation of Conjugate of IL-2 With Fractionated Polyproline

A. Preparation and Characteristics of Conjugate

A total of 3 g of polyproline was fractionated on a Sephacryl 200 size exclusion chromatograph in 0.1M sodium phosphate buffer at pH 7.0. Five pooled fractions at five different $A_{225}$ absorbance levels (about 20 ml each) were placed in dialysis tubing with a molecular weight cut-off of 3,500. These fractions were dialyzed against deionized water in separate 2-liter cylinders for three changes, one after about two hours, one after one hour, and the last overnight. The fractions were lyophilized after one more change of one hour. Each fraction was then weighed and the amount of fractionated polyproline in each was determined.

One of the polyproline fractions from the second half of the peak was used to prepare an active ester using the method described in Example 1.A. The activated ester was then conjugated to IL-2 as described in Example 1.

The IL-2 conjugate was found to have the same activity as the unmodified IL-2, as measured by the test described in Example 1.

The IL-2 conjugate was purified as described in Example I and found to be soluble in water without SDS at room temperature for greater than one week. The IL-2 conjugate had no free IL-2, as determined by SDS-PAGE with silver staining.

B. Pharmacokinetics of Conjugate

Pharmacokinetic data of unmodified IL-2 and the IL-2 modified with fractionated polyproline (determined by HPLC sizing to have an apparent molecular weight of about 44,000 daltons) were obtained after intravenous administration of 250 µg/kg of protein into a lateral tail vein of each rat in a total of five rats. A Silastic cannula had been placed in the right jugular vein under ketamine anesthesia on the previous day. At various later times after injection 150 µl blood samples were removed from the jugular vein cannula into heparinized capillary tubes. Plasma was prepared immediately by centrifugation for three minutes and an aliquot was diluted into assay medium for bioassay as described in Example I.

Figure 1:
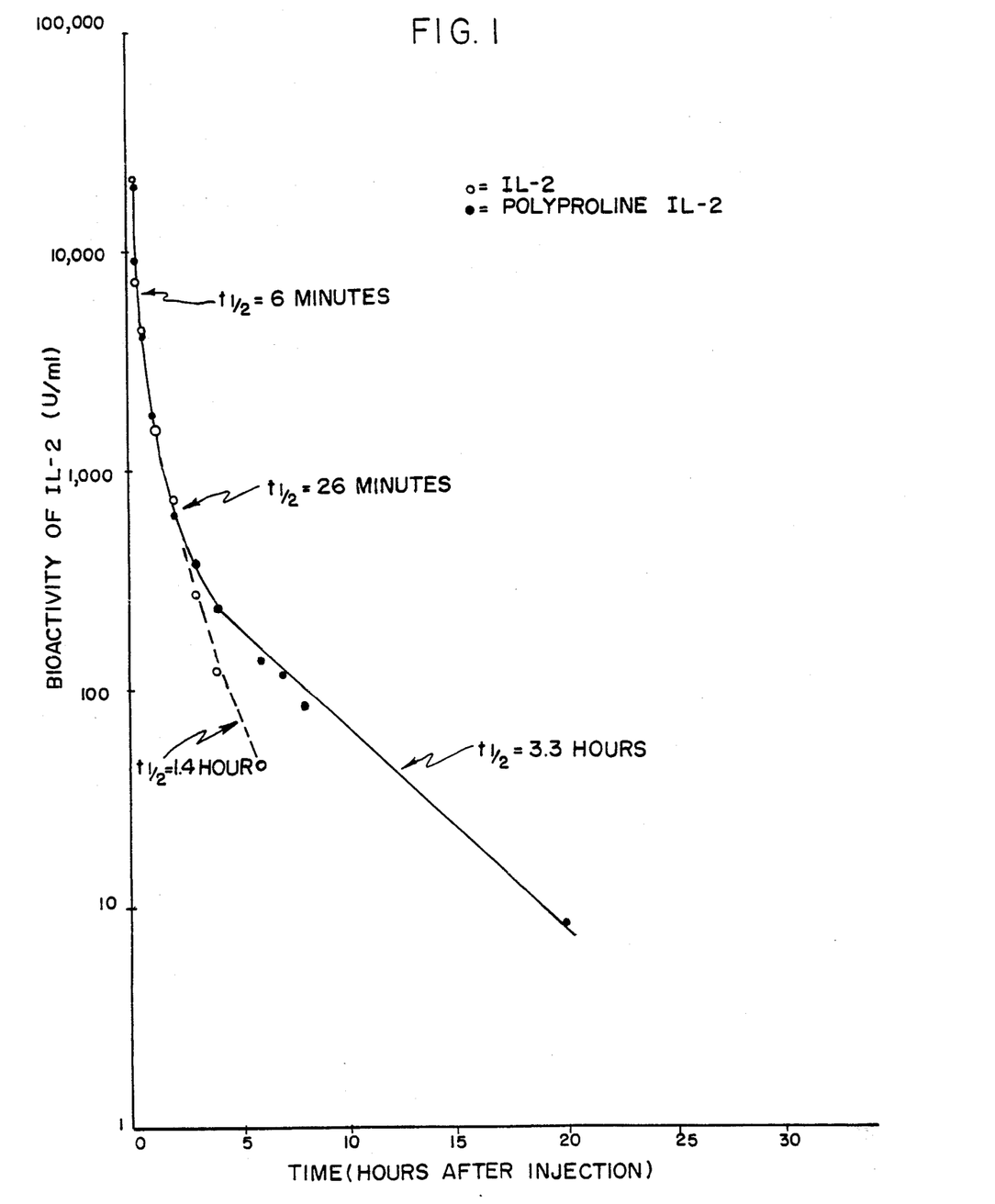
FIG. 1 depicts blood plasma curves of unmodified IL-2 and IL-2 modified with polyproline after intravenous injection into rats.

FIG. 1 shows the pharmacokinetics of the average values for unmodified IL-2 and IL-2 modified with the fractionated Polyproline. The half-lives at three slopes of the blood plasma curves of FIG. 1 are the following:

| Sample | $t_{\frac{1}{2}}$ (8000 U/ml) | $t_{\frac{1}{2}}$ (800 U/ml) | $t_{\frac{1}{2}}$ (80 U/ml) |
|---|---|---|---|
| Unmodified IL-2 | 4 min. | 28 min. | 1.4 hr. |
| IL-2 modified with polyproline | 6 min. | 26 min. | 3.3 hr. |

Thus, on initial and second phase distribution of both Proteins the circulating half-life is the same, as measured by cell proliferation assays, but in the third phase the half-life is longer for the IL-2 modified with polyproline. It is expected that a modified IL-2 of a larger apparent molecular weight than 44,000 daltons may yield an even longer half-life in vivo.

In summary, the present invention is seen to provide a pharmaceutical composition wherein certain biologically active proteins are covalently conjugated to polyproline via a spacer arm and thereby made more soluble in an aqueous medium at physiological pH. The conjugation serves to solubilize the normally hydrophobic poorly water-soluble protein in water at pH 6-8 and to retain or enhance its biological activity. Without the conjugation, the protein must be solubilized by addition of solubilizing agents such as detergents or denaturants, or by raising or lowering the pH in combination with addition of a stabilizer.

Various modifications of the above-described modes for carrying out the invention which are obvious to those skilled in the field of protein and organic chemistry and pharmaceutical formulation or related fields are intended to be within the scope of the following claims.

What is claimed is:

1. A pharmaceutical composition comprising a non-toxic, inert, pharmaceutically acceptable aqueous carrier medium in which is dissolved a biologically active protein, selected from the group consisting essentially of interferons, interleukins, colony stimulating factors, and immunotoxins, covalently conjugated via a flexible spacer arm to polyproline, wherein said protein in its unconjugated form is not readily soluble in said aqueous carrier medium at pH 6-8 in the absence of a solubilizing agent.

2. The composition of claim 1 wherein said polyproline has a molecular weight of 1000 to 100,000.

3. The composition of claim 2 wherein said polyproline has a molecular weight of 2000 to 40,000.

4. The composition of claim 1 wherein said spacer arm is where a is at least 1, x is 2-4, y is 2-4, z is 2-4, and n is 1-10.

5. The composition of claim 1 wherein the medium is at a pH of about 5-8 and contains a buffer.

6. The composition of claim 1 wherein the medium is at a pH of 6.5-7.8 and contains a buffer.

7. The composition of claim 1 wherein the protein is selected from the group consisting of interleukin-2, β-interferon, CSF-G, CSF-GM, CSF-1 and an immunotoxin.

8. The composition of claim 1 wherein the protein is a recombinant protein with an amino acid sequence from a human source.

9. The composition of claim 8 wherein the protein is produced from a microbial host.

10. The composition of claim 8 wherein the protein is interleukin-2 or a rutein thereof.

11. The composition of claim 10 wherein said IL-2 mutein is human IL-2 and has the amino acid(s) that are at position(s) 104 and/or 125 in the native protein substituted with a neutral amino acid and/or from 1 to 5 of the first five amino acids at the N-terminus of the native protein deleted.

12. The composition of claim 11 wherein said mutein is $ser_{125}$ IL-2, $des\text{-}ala_{11}$L-2, $des\text{-}alaIser_{125}$ IL-2, $des\text{-}ala_1ala_{1041}$L-2, or $des\text{-}ala_1alaI04ser_{125}$ IL-2.

13. The composition of claim 7 wherein said protein is a β-interferon or a mutein thereof.

14. The composition of claim 1 wherein said mutein has the cysteine residue at position 17 in the native protein substituted with a neutral amino acid and/or from 1 to 5 of the first five amino acids at the N-terminus of the native protein deleted.

15. The composition of claim 10 wherein said mutein is $ser_{17}$ IFN-β.

16. The composition of claim 1 wherein said immunotoxin includes a recombinant Ricin A chain.

* * * * *